United States Patent [19]

Takashima et al.

[11] Patent Number: 5,365,930
[45] Date of Patent: Nov. 22, 1994

[54] APPARATUS FOR MEASURING AND EVALUATING BLOOD CIRCULATION

[75] Inventors: Mitsuru Takashima; Yoshiki Satoh, both of Tokyo, Japan

[73] Assignee: Sony Corporation, Japan

[21] Appl. No.: 851,662

[22] Filed: Mar. 16, 1992

[30] Foreign Application Priority Data

Mar. 18, 1991 [JP] Japan .................................. 3-077269

[51] Int. Cl.$^5$ ............................................ A61B 5/021
[52] U.S. Cl. .................................. 128/672; 128/687; 128/690
[58] Field of Search .................. 128/672, 677–686, 128/687–690

[56] References Cited

U.S. PATENT DOCUMENTS

| | | |
|---|---|---|
| 3,704,528 | 12/1972 | Lewis . |
| 4,066,066 | 1/1978 | Paek .................................. 128/2.05 |
| 4,442,845 | 4/1984 | Stephens ............................ 128/687 |
| 5,005,581 | 4/1991 | Honeyager ...................... 128/672 X |

FOREIGN PATENT DOCUMENTS

| | | |
|---|---|---|
| 0032159 | 7/1981 | European Pat. Off. . |
| 57-52054 | 11/1982 | Japan . |
| 651540 | 4/1951 | United Kingdom . |
| 1108652 | 4/1968 | United Kingdom . |

Primary Examiner—Angela D. Sykes
Attorney, Agent, or Firm—Ronald P. Kananen

[57] ABSTRACT

An apparatus for observing and evaluating blood circulation utilizing pressure sensors disposed along an artery. Three pressure sensors may be used to detect pulses at the shun, khan, and shaku spots of the sunko as in the practice of Oriental medicine. In one embodiment observing blood circulation, a first pressure sensor detects a pulse in the artery on a heart side and a second pressure sensor detects an artery pulse between the heart side and a peripheral side. First and second level detecting means detect when the respective first and second pressure signals exceed predetermined levels and provide output signals to a measuring means. A biasing pressure controlling means controls the biasing force exerted by a biasing means upon the blood flow through the artery and is responsive to the output of the second level detecting means. The measuring means measures a first period of time after the first level detecting means detects that the first pressure signal exceeds a predetermined level and a second period of time from when a notch occurs in the first pressure signal until a notch occurs in the second pressure signal. Information on blood viscosity, artery hardness, and inner wall condition is also obtained.

26 Claims, 8 Drawing Sheets

FIG.1

*(PRIOR ART)*

APPARATUS FOR MEASURING AND EVALUATING BLOOD CIRCULATION

BACKGROUND OF THE INVENTION (a) Field of the Invention

The present invention relates to an observation apparatus, and in particular to an apparatus for observing the blood circulating function of a patient with no contact with the blood by observing the waveform of the arterial pulses.

(b) Prior Art

Cardiographic or ultrasonic tomographic diagnosis apparatus has heretofore been used for examination of the heart disease.

Since the arterial pulses related with the motion of the heart contain important information representative of the condition of the blood circulating function, they are widely used for determining whether or not the blood circulating function is good. Observation of the volumetric pulses representative of the content of blood in the capillary vessels has generally been conducted.

A method of converting changes in pressure due to the heart beat into electrical signals by using a piezo-electric element or capacitor microphone or a method for optically detecting changes in the amount of blood flow by using optical modulating action of hemoglobin in blood have been adopted for detecting the arterial pulses.

In Oriental medicine, the conditions of a patient are determined by sphygmic diagnosis solely relying on the sense of touch of the arterial pulses on the "sunko", that is, the processus styloideus radii on the inner side of the wrist. In the sphygmic diagnosis of Oriental medicine, the pulses on the "sunko" are classified into those on three spots, such as upper, middle and lower spots which are referred to as "shun", "khan" and "shaku", respectively and two kinds of pulsation condition "myakki" on the pulse route "keimyaku" appeared on respective spots are sensed.

The term "shun" means the heart side of the artery of the wrist. The pulses on the "shun" represent the health conditions of the patient from the head to the chest. The term "khan" means the middle artery of the wrist between the distal end and the heart. The pulses on the "khan" represents the health conditions between the chest and the navel. The term "shaku" means the distal end side of the artery in the wrist and the pulses on the "shaku" represents the health conditions between the navel and the toe.

A sphygmic diagnosis apparatus in which arterial pulses are detected from the artery of a human being by means of sensors such as an infrared ray sensor or a pressure sensor for performing the diagnosis by observation of the sphygmogram has heretofore been known as is disclosed in the specification of the Japanese Examined Patent Publication No. 57-52054.

Figure 1:
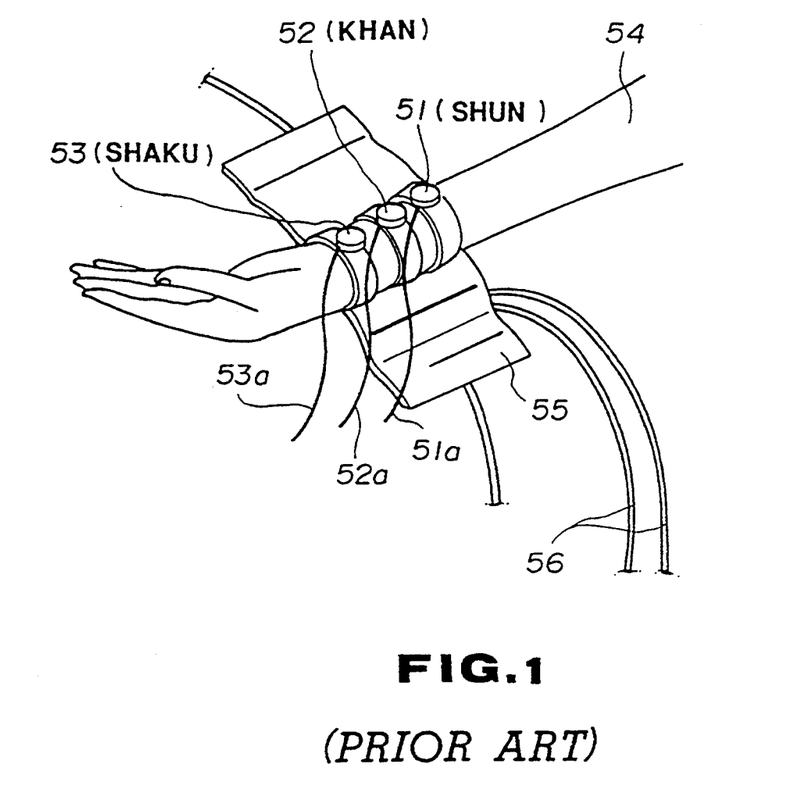
FIG. 1 is a perspective view showing a vascular wave detecting means for detecting the pulses of the shun, khan and shaku of the sunko in Oriental medicine.

The disclosed diagnosis apparatus comprises three pressure sensor 51, 52 and 53 for converting the arterial pulses on the three spots such as "shun", "khan" and "shaku" of the "sunko" into electrical signal waves and a cuff band 55 which is mounted on the wrist 54 of a patient for biasing the pressure sensors 51, 52 and 53 upon the artery of the wrist as shown in FIG. 1.

The pressure sensors 51, 52 and 53 are disposed on the wrist 54, that is, on and along the artery in the "sunko" and the cuff 55 is wrapped around the wrist. A compressed air is pumped into an air bag (not shown) provided on the cuff 55 from a pneumatic pump via a conduit 56. The arterial pulses can be measured by adjusting the amount of the pumped air to change the pressure applied upon the artery.

The pressure sensors 51, 52 and 53 comprise, for example, so-called electrostatic microphones or piezo-electric microphones. Specifically, in case of the electrostatic microphone, a high d.c. voltage is applied across an electrode of a vibrating plate and a fixed electrode of the vibrating plate is brought into direct contact with a spot on which a pressure is detected, for example the artery of the "sunko". The spacing between the electrode of the vibrating plate and the fixed electrode is changed due to pressure to change the electrostatic capacity therebetween. The voltage generated at this time is detected. The pressure sensors 51, 52 and 53 are connected with an electromagnetic oscillograph and the like through connection codes 51a, 52a and 53a respectively so that the measured arterial pulses are recorded on a recording paper and the like for observing the sphygmogram.

Although the cardiography or ultrasonic tomography has been used for examination of heart disease as mentioned above, it is very hard to quantitatively diagnose the condition of the heart disease by observing the condition of the blood circulating function with no contact with the blood. Confirmation of an abnormality has been visually carried out by well experienced medical doctors.

There has been no means for measuring the viscosity of the blood in the artery which is changed by the disease of the internal organs such as heart disease or liver disease except for the blood circulating function for examining the heart disease. Information on the viscosity of blood can not be used for diagnosis of the disease of the internal organs.

It is hard to observe the hardness of the artery, which changes with an advance in the heart disease, with no contact with the blood. A method of estimating the hardness of the artery by pressing a sensor for investigating the relation between stress and strain upon the radial artery has been known as a method of measuring the hardness of the artery without contacting blood. However, this method is strongly influenced by the tissue between the artery and the upper skin. Accordingly, this method is inaccurate so that the hardness of the artery can not be quantified.

OBJECT AND SUMMARY OF THE PRESENT INVENTION

Therefore, the present invention was made in view of such circumstances.

It is a first object of the present invention to provide a blood circulating function observing apparatus which is capable of properly determining the condition of the blood circulating function of a patient with no contact with the patient's blood.

It is a second object of the present invention to provide a blood viscosity observing apparatus which is capable of properly observing the viscosity of the blood in the artery of a patient with no contact with the patient's blood.

It is a third object of the present invention to provide an artery hardness observing apparatus which is capable of properly observing the hardness of the artery of a patient with no contact with the patient's blood.

DESCRIPTION OF EMBODIMENTS

An embodiment of a blood circulating function observing apparatus of the present invention will be described in detail with reference to the drawings.

Figure 2:
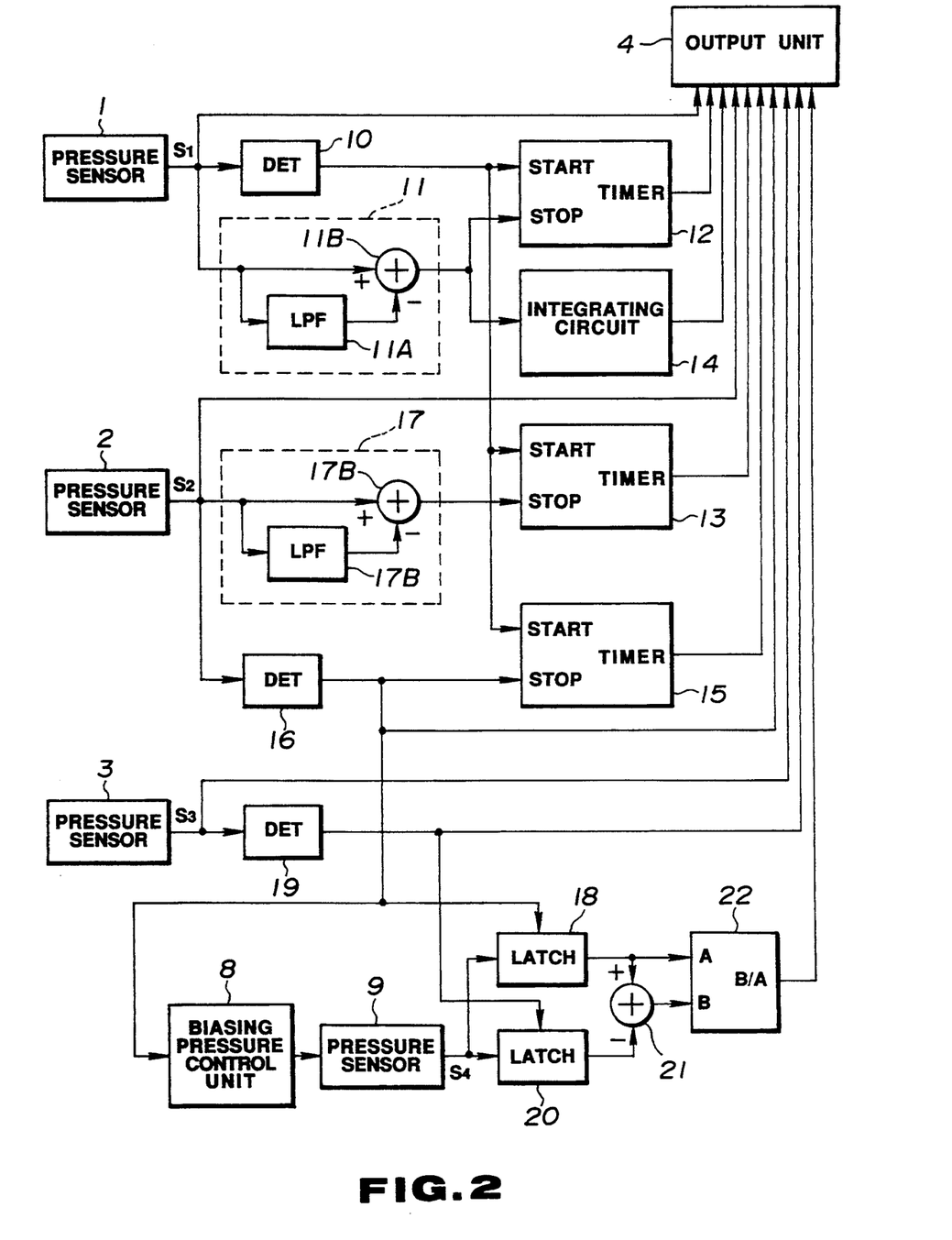
FIG. 2 is block diagram showing the structure of a sphygmic diagnosis apparatus in accordance with the present invention.

The blood circulating function observing apparatus of the present invention is formed as shown in FIG. 2.

The blood circulating function observing apparatus of the present invention is applied to a sphygmic diagnosis apparatus which determines the disease of a patient by detecting the arterial pulses at spots such as "shun", "khan", "shaku" of "sunko" in Oriental medicine. The observing apparatus comprises first to third pressure sensors 1, 2 and 3 which detect the arterial pulses of "shun, "khan", "shaku" of the sunko and convert them into electrical signals. Output signals $S_1$, $S_2$ and $S_3$ from the pressure sensors 1, 2 and 3 are supplied to an output unit 4 for observing the waveforms of the detection output signals $S_1$, $S_2$ and $S_3$. The output unit 4 may be a display for displaying the waveforms of the signals $S_1$, $S_2$ and $S_3$ on a screen or a printer for printing the waveforms of the detected output signals $S_1$, $S_2$ and $S_3$ on a recording paper.

Figure 3:
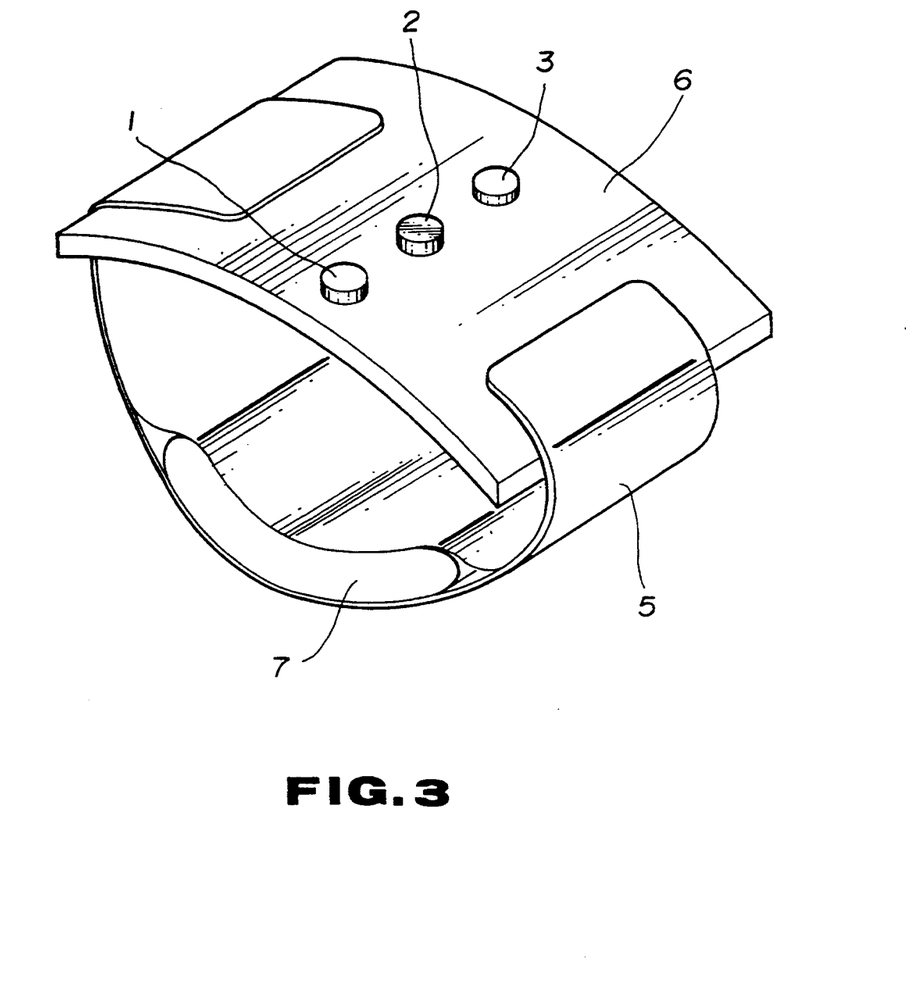
FIG. 3 is a perspective view showing the disposition of three pressure sensors in the sphygmic diagnosis apparatus shown in FIG. 2.
Figure 4:
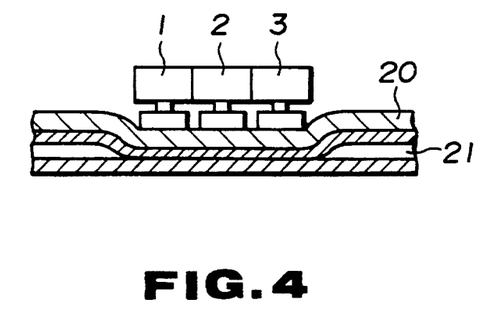
FIG. 4 is a sectional view showing the biasing upon the artery by the three pressure sensors in the sphygmic apparatus shown in FIG. 2.

The first to third pressure sensors 1, 2 and 3 comprise pressure-electric converting elements such as piezoelectric microphones for detecting the arterial pulses of the shun, khan and shaku of the sunko as changes in pressure. The first to third pressure sensors 1, 2 and 3 are disposed on the inner wall of a fixing plate 6 having opposite ends which are connected each other via a cuff band 5 which will be worn around the wrist of a patient as shown in FIG. 3. The first to third pressure sensors 1, 2 and 3 are pressed upon the positions of detection corresponding to the shun, khan and shaku of the sunko in Oriental medicine by the admission of air into an air bag 7 provided on the cuff band 5 for pressing a skin tissue 20 of the wrist of the patient to block an artery 21.

Air is charged into or from the air bag 7 provided in the cuff band 5 from an air pump (not shown) which is controlled by a biasing control unit 8 and the air is discharged via an exhaust valve (not shown) which is controlled by the biasing control unit 8. The biasing pressure supplied by the first to third pressure sensors 1, 2 and 3 of the air bag 7 are detected by a fourth pressure sensor 9.

The first pressure sensor 1 which detects the shun of the sunko, i.e. the artery pulse on the side of the heart, supplies the detection output signal $S_1$ to the output unit 4 and to a first level detecting circuit 10 and a notch detecting circuit 11.

The first level detecting circuit 10 detects when the detection output signal $S_1$ from the first pressure sensor 1 assumes a predetermined output level. A detection output signal from the first level detecting circuit 10 is supplied to first and third timer circuit 12 and 15 as a timer start signal.

The first notch detecting circuit 11 detects a notch (omitted portion of the waveform) contained in the arterial pulses on the side of the heart, i.e in the detection output signal $S_1$ from the first pressure sensor 1. The first notch detecting circuit 11 comprises a low pass filter 11A for extracting a fundamental wave component of the detection output signal $S_1$ from the first pressure sensor 1 and a subtracter 11B for subtracting the fundamental wave component extracted by the low pass filter 11A from the detection output signals of the first pressure sensor 1. A first notch signal which is obtained as the subtraction output signal from the subtracter 11B is supplied to the first timer circuit 12 as a timer stop signal and to an integrating circuit 14 and to a second timer circuit 13 as a timer start signal.

The first timer circuit 12 measures a period of time from when the first level detecting circuit 10 detects that the detection output signal $S_1$ having a level higher than a predetermined level is obtained until the first notch detecting circuit 11 detects the notch contained in the detection output signal $S_1$ from the first pressure sensor 1. A measurement output signal from the first timer circuit 12 is supplied to the output unit 4. The integrating circuit 14 integrates the first notch detection signal from the first notch detecting circuit 11. The integration output signal from the integrating circuit 14 is supplied to the output unit 4.

The second pressure sensor 2 which detects the khan of the sunko, i.e. the artery pulse between the heart and peripheral side supplies the detection output signal $S_2$ to the output unit 4 and to a second level detecting circuit 16 and a notch detecting circuit 17.

The second level detecting circuit 16 detects when the detection output signal $S_2$ from the second pressure sensor 2 reaches a predetermined output level. An output signal from the second level detecting circuit 16 is supplied to the output unit 4 and the biasing control unit 8 and to a third timer circuit 15 as a timer stop signal and to a first latch circuit 18 as a first latch signal.

The third timer circuit 15 measures a period of time from when the first level detecting circuit 10 detects that the detection output signal $S_2$ having a level higher than a predetermined level is obtained until the second level detecting circuit 10 detects that the detection output signal $S_2$ higher than a predetermined level is obtained from the second pressure sensor 2. A measurement output signal from the third timer circuit 15 is supplied to the output unit 4.

The second notch detecting circuit 17 detects a notch (omitted portion of the waveform) contained in the detection output signal $S_2$ from the second pressure sensor 2, i.e. in the arterial pulses between the heart and the peripheral sides. The second notch detecting circuit 17 comprises a low pass filter 17A for extracting a fundamental wave component of the detection output signal $S_2$ from the second pressure sensor 2 and a subtracter 17B for subtracting the fundamental wave component extracted by the low pass filter 17A from the detection output signal $S_2$ of the second pressure sensor 2. A second notch signal which is obtained as the subtraction output signal from the subtracter 17B is supplied to a second timer circuit 13 as a timer stop signal.

The second timer circuit 13 measures the period of time from when the first notch detecting circuit 11 detects a notch contained in the detection output signal $S_1$ from the first pressure sensor 1 until the second notch detecting circuit 17 detects a notch contained in the detection output signal $S_2$ from the second pressure sensor 2. A measurement output signal from the second timer circuit 13 is supplied to output unit 4.

The third pressure sensor 3 which detects the shaku of sunko, i.e. the arterial pulse on the peripheral side supplies the detection output signal $S_3$ to the output unit 4 and to a third level detecting circuit 19.

The third level detecting circuit 19 detects when the detection output signal $S_3$ from the third pressure sensor 3 reaches a predetermined output level. The detection output signal from the third level detecting circuit 19 is supplied to a second latch circuit 20 as a second latch signal.

The fourth pressure sensor 9, which detects the biasing forces of the first to third pressure sensors 1, 2 and 3 excepted by the air bag 7, supplies the detection output signal $S_4$ to the first and second latch circuits 18 and 20.

The first latch circuit 18 latches the detection output signal $S_4$ from the fourth pressure sensor 9 in response to the first latch signal, i.e. the detection output signal from the second level detecting circuit 16 and supplies the latch output signal to a subtracter 21 and a divider 22. The latch output signal from the first latch circuit 18 represents the blood flow full passage pressure P1 at which the detection output signal $S_2$ not less than a predetermined level is obtained from the second pressure sensor 2.

The second latch circuit 20 latches the detection output signal $S_4$ from the fourth pressure sensor 9 in response to the second latch signal, i.e. the detection output signal from the third level detecting circuit 19 and supplies the latch output signal to a subtracter 21.

The latch output signal from the second latch circuit 20 represents the blood flow full passage pressure P2 at which the detection output signal $S_3$ not less than a predetermined level is obtained from the third pressure sensor 3.

The subtracter 21 subtracts the latch output signal from the second latch circuit 20 from the latch output signal from the first latch circuit 18 and supplies the subtraction output, signal to the divider 22. The subtraction output signal from the subtracter 21 represents a pressure difference $P_1-P_2$ which is a difference between the blood flow full passage pressure $P_1$ at which the blood fully passes through the first, pressure sensor 1 represented by the latch output signal from the first latch circuit 18 and the blood flow full passage pressure $P_2$ at which the blood fully passes through the second pressure sensor 2 which is represented by the latch output signal from the second latch circuit 20.

The divider 22 normalizes the pressure difference $P_1-P_2$ which is represented by the subtraction output signal by dividing the subtraction output signal of the subtracter 21 by the latch output signal from the first latch circuit 18. The detection output signal from the division output signal from the divider 22, i.e. the normalized pressure difference $(P_1-P_2)/P_1$ from the divider 22 is supplied to the output unit 4.

The sphygmic diagnosis apparatus which is formed in such a manner is used in selected one of first to third operative modes.

In the first operation mode, the biasing force of the first to third pressure sensors 1, 2 and 3 by the air bag 7 is gradually changed from the blood flow blocked condition to the full passage condition by controlling a pneumatic pump and an exhaust valve (not shown) by the biasing pressure control unit 8. The waveshape of each of the detection output signals $S_1$, $S_2$ and $S_3$ of the first to third pressure sensors 1, 2 and 3 is observed. Accordingly, the disease of the patient can be diagnosed by observing the arterial pulses of the shun, khan and shaku of the sunko in the Oriental medicine.

Figure 5:
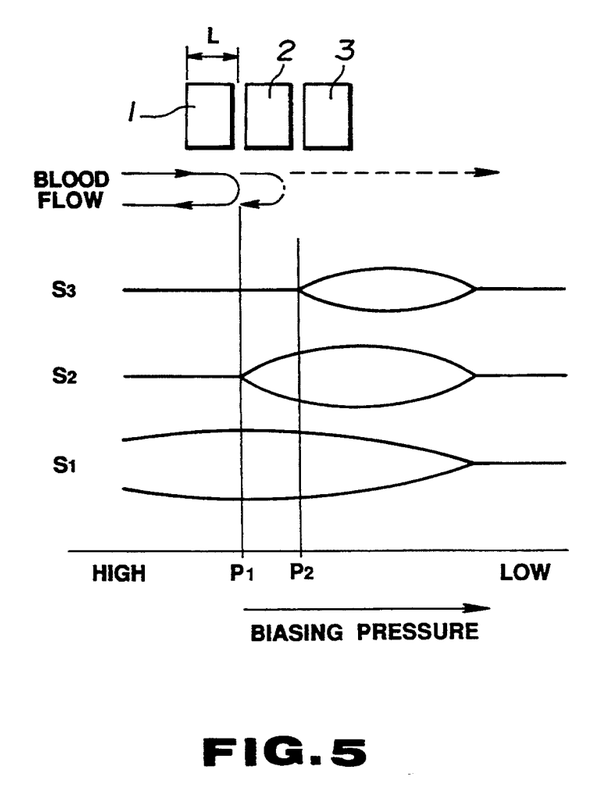
FIG. 5 is a graph showing the changes in the levels of the detection output signals which are obtained by the three pressure sensors in the sphygmic diagnosis apparatus shown in FIG. 2.

If the biasing force of the first to third pressure sensors 1, 2 and 3 exerted by the air bag 7 is gradually changed from the blood flow blocked condition to the full passage condition, the level of the detection output signal $S_1$ of the first pressure 1 which is located on the side of the heart is first elevated and then the level of the detection output signal $S_2$ of the second pressure sensor 2 which is located in the intermediate position is elevated and finally the level of the detection output signal $S_3$ of the third pressure sensor 3 which is located in the terminal position is elevated as shown in FIG. 5. If the biasing force is lowered, the levels of the detection output signals $S_1$, $S_2$ and $S_3$ of the first to third pressure sensors 1, 2 and 3 are simultaneously lowered.

In the second operation mode, the biasing force of the first to third pressure sensors 1, 2 and 3 exerted by the air bag 7 is gradually lowered from the blood flow blocked condition and the pneumatic pump and the exhaust valve (not shown) are controlled by the biasing force control unit 8 in response to the detection output signal from the second level detecting circuit 16 so that the biasing pressure $P_1$ is maintained constant on a blood flow passage restricted condition on which the detection output signal can be obtained from the second level detecting circuit 16.

Figure 6:
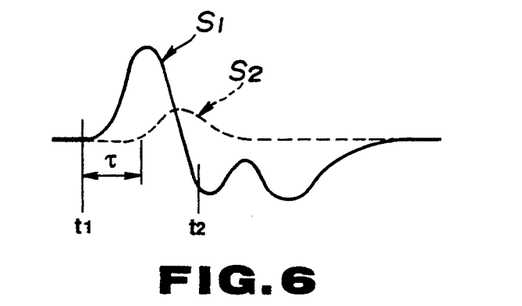
FIG. 6 is a waveform chart showing the waveforms of the detection output signals obtained by the first and second pressure sensors in the sphygmic diagnosis apparatus shown in FIG. 2.

On the blood flow passage restricted condition, each of the detection output signals $S_1$ and $S_2$ obtained by the first and second pressure sensors 1 and 2 have a smooth continuous sinusoidal waveform from the $t_1$ when the ventricle of the heart begins to contract to the time $t_2$ when the aorta valve closes as shown in FIG. 6 in which the waveforms of the detection output signals $S_1$ and $S_2$ of the first and second pressure sensors 1 are depicted by the solid dotted lines, respectively if the blood circulating function of the patient is normal.

Figure 7:
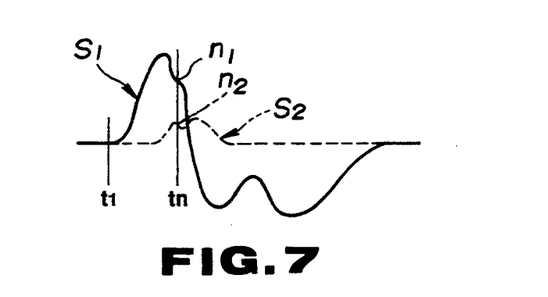
FIG. 7 is a waveform chart showing the waveform representative of an abnormality in pressure of the blood circulating function observed in the sphygmic diagnosis apparatus shown in FIG. 2.
Figure 8:
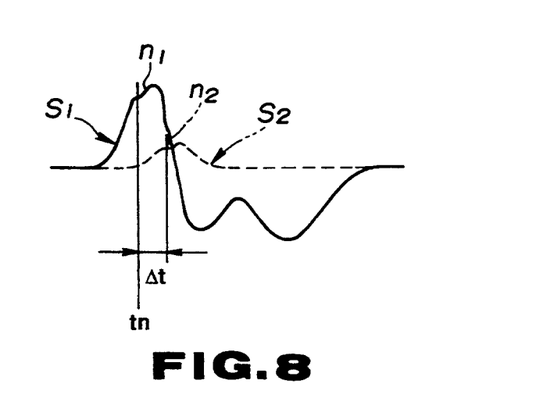
FIG. 8 is a waveform chart showing the waveform representative of an abnormality in blood flow of the blood circulating function observed in the sphygmic diagnosis apparatus shown in FIG. 2.

In contrast to this, the blood circulating function of the patient is abnormal, a notch occurs at an interval from the time $t_1$ when the ventricle of the heart begins to contract and the time $t_2$ when the aorta valve closes. If there is an abnormality of the fast pressure propagation due to valve abnormality, notches $n_1$ and $n_2$ appear at the substantially same time $t_n$ as shown in FIG. 7 in which the waveforms of the detection output signals $S_1$ and $S_2$ are depicted by the solid and dotted lines, respectively. If there is an abnormality of the slow propagation flow due to abnormality in the heart muscle, notches $n_1$ and $n_2$ appear at times having a time difference $\Delta t$ therebetween as shown in FIG. 8 in which the wave forms of the detection output signals $S_1$ and $S_2$ of the first and second pressure sensors 1 and 2 are depicted by solid and dotted lines, respectively When the present sphygmic diagnosis apparatus is in the second operation mode, first timer circuit 12 measures the period of time $t_n$ from the time $t_1$ when the ventricle of the heart begins to contract until the notch $n_1$ appears in the detection output signal $S_1$ of the first pressure sensor 1 and the second timer circuit 13 measures the period of time since the notch $n_2$ appears in the detection output signal of the first pressure sensor 1 until the notch $n_2$ appears in the detection output signal $S_2$ of the second pressure sensor 2, i.e. the time difference $\Delta t$ of the notches $n_1$ and $n_2$ and the output unit 4 outputs the time information $t_n$ and $\Delta t$ of the notches $n_1$ and $n_2$.

The measurement data $t_n$, $\Delta t$ of the first and second timer circuits 12 and 13 are outputted from the output unit 4 as blood flow circulating function observing data in such a manner. Therefore, the blood circulating function condition of the patient can be properly diagnosed in non-contact with blood without any experiences.

The disease condition can be quantified by determining the size (area) of the notch n by integrating in the integrating circuit 14 the first notch detection signal from the first notch detecting circuit 11 which detects the notch $n_1$ appearing in the detection output signal $S_1$ of the first pressure sensor 1. Diagnosis of the disease can be more properly performed by displaying or printing the integration output signal from the integrating circuit 14 as blood circulating function observing data.

In the second operation mode, the third timer circuit 15 measures the period of time since the first level detector 10 detects that the detection output signal $S_1$ not less that a predetermined level is obtained by the first pressure sensor 1 until the second level detecting circuit 16 detects that the detection output signal $S_2$ not less than a predetermined level is obtained from the second pressure sensor 2, i.e. the time which is taken for the blood to move by a distance L between the first and second pressure sensors 1 and 2.

The velocity v at which the blood moves through the first pressure sensor 1 on the blood flow passage restricted condition is represented by equation 1.

$$v \propto 1/\mu \qquad (1)$$

wherein $\mu$ represents the viscosity of blood.

Since the velocity of the blood depends upon the blood viscosity $\mu$, the viscosity can be estimated by measuring the time $\tau$ which is taken for the blood to move by a distance L between the first and second pressure sensors 1 and 2.

The output unit 4 to which the detection output signal is supplied from the third timer circuit 15 outputs the measurement $\tau$ which is taken for the blood move by a distance L between the first and second pressure sensors 1 and 2 as a measurement data of the blood viscosity $\mu$. Accordingly, information on the blood viscosity which is obtained by normalizing the arterial blood viscosity $\mu$ can be obtained in no contact manner with blood.

Figure 9:
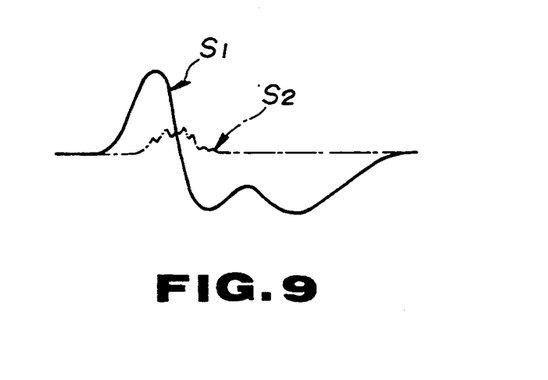
FIG. 9 is a chart showing the representative of the inner wall condition of a blood vessel observed by the sphygmic diagnosis apparatus shown in FIG. 2.

In the second operation mode, the waveforms of a comparison output signal between a reference waveform signal based upon the detection output signal $S_1$ from the first pressure sensor 1 and the detection output signal $S_2$ from the second pressure sensor 2 is displayed or printed out by the output unit 4 as observation information on the condition of the inner wall of the blood vessel the blood which moves through the first pressure sensor 1 on the blood flow passage restricted condition as a thin film flow exhibits a wave surface (representing the elevation and lowering of pressure) depending upon the roughness of the inner wall of the artery. The detection output signal $S_2$ from the second pressure sensor 2 has a waveform depending upon the roughness of the inner wall of the artery as shown, in FIG. 9. Accordingly, information on the roughness of the inner wall of the artery can be obtained in a no contact manner with the blood.

In the second operation mode, the waveform of each of the detection output signals $S_1$ and $S_2$ from the first pressure sensor 1 on the heart side and the intermediate second pressure sensor 2 is observed. Since there is provided the third pressure sensor 3 on the peripheral side, accurate waveform observation can be made by removing the influences of the blood on the peripheral side.

In the third operation mode, the pneumatic pump and exhaust valve (not shown) are control led by the biasing control unit 8 so that the biasing force of the first to third pressure sensors 1, 2 and 3 exerted by the air bag 7 is gradually lowered from the blood flow blocked condition. Information on the normalized pressure difference $(P_1-P_2)/P_1$ represented by the division output signal from the divider 22 is outputted from the output unit as obtained information on the hardness of the artery.

When the first to third pressure sensors 1, 2 and 3 are closely disposed along the artery in a similar manner to this sphygmic apparatus, loads exerted by the first pressure sensor located on the heart side and the third pressure sensor 3 on the peripheral side give an influence upon the intermediate blood vessel on which the second pressure sensor 2 is located so that the central load increases. The increase in load has a positive correlation with the hardness of artery of the wrist of the patient which biases the first to third pressure sensors 1, 2 and 3. The pressure difference $P_1-P_2$ between the blood flow full passage pressure $P_1$ at which the blood fully passes through the first pressure sensor 1 on the heart side and the blood full passage pressure $P_2$ at which the blood fully passes through the intermediate second pressure sensor 2 can be used as information representative of the hardness of the artery of the wrist of the patient. Since the blood flow full passage pressure point is a point where the load is balanced with the maximum blood pressure via the skin tissue, the pressure difference $P_1-P_2$ is hardly influenced by the differences of blood pressure or skin tissues among persons.

In accordance with the present embodiment, the pressure difference $P_1-P_2$ is displayed or printed out by the output unit 4 as observation information on the hardness of the artery having differences among persons due to blood pressure, etc. by normalizing the pressure difference by the divider 22. Accordingly, observation information on the hardness of the artery can be obtained in a no contact manner with blood.

In accordance with the observing apparatus of the present invention shown in FIGS. 2 to 9, observation of the blood circulating function, the viscosity of the blood, and the hardness of the artery of a patient can be performed in the output unit by observing the waveform of the arterial pulses.

However, information on the arterial pulse in the wrist can not be obtained by techniques relating to an artificial heart and valves therefor which are provided for the simulation device for the human blood circulating system. Simulation of pulses in positions of shun, khan and shaku of the Oriental medicine has been impossible. A sphygmic diagnosis simulation blood circulating system which can obtain the arterial pulses will be described with reference to the drawings.

Figure 10:
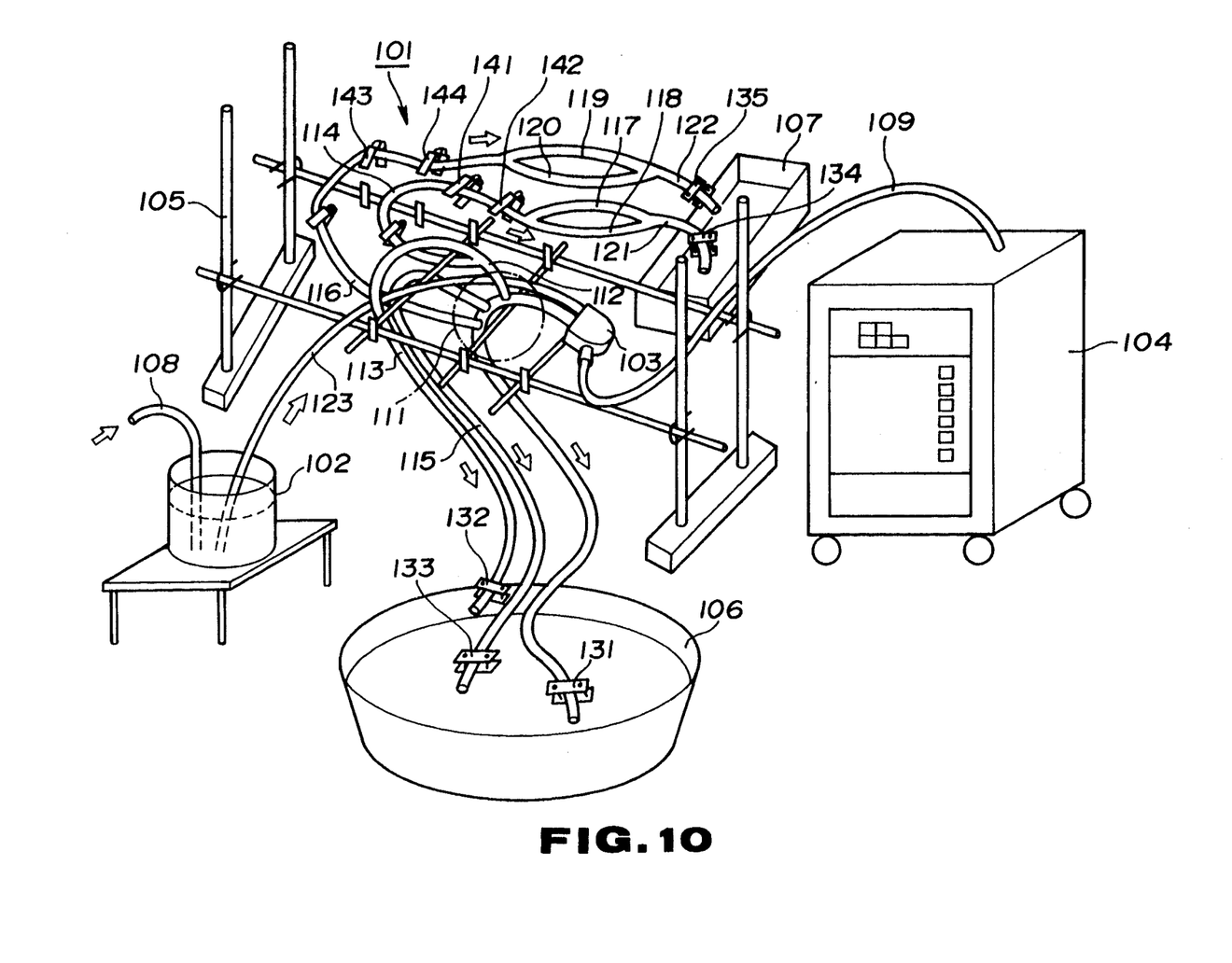
FIG. 10 is a view showing the appearance of a simulated blood circulating apparatus of the present invention.

A simulated blood circulating apparatus comprises a simulated blood circulating passage 101 in which the blood circulating system of a human body is simulated, an atrium portion reservoir 102 for reserving the simulated blood which flows through the simulated blood circulating passage 101, an artificial heart unit 103 for supplying the simulated blood reserved in the atrium portion reservoir 102 to the simulated blood circulating passage 101, and an artificial heart driving unit 104 for driving the artificial heart unit 103 as shown in FIG. 10.

Figure 11:
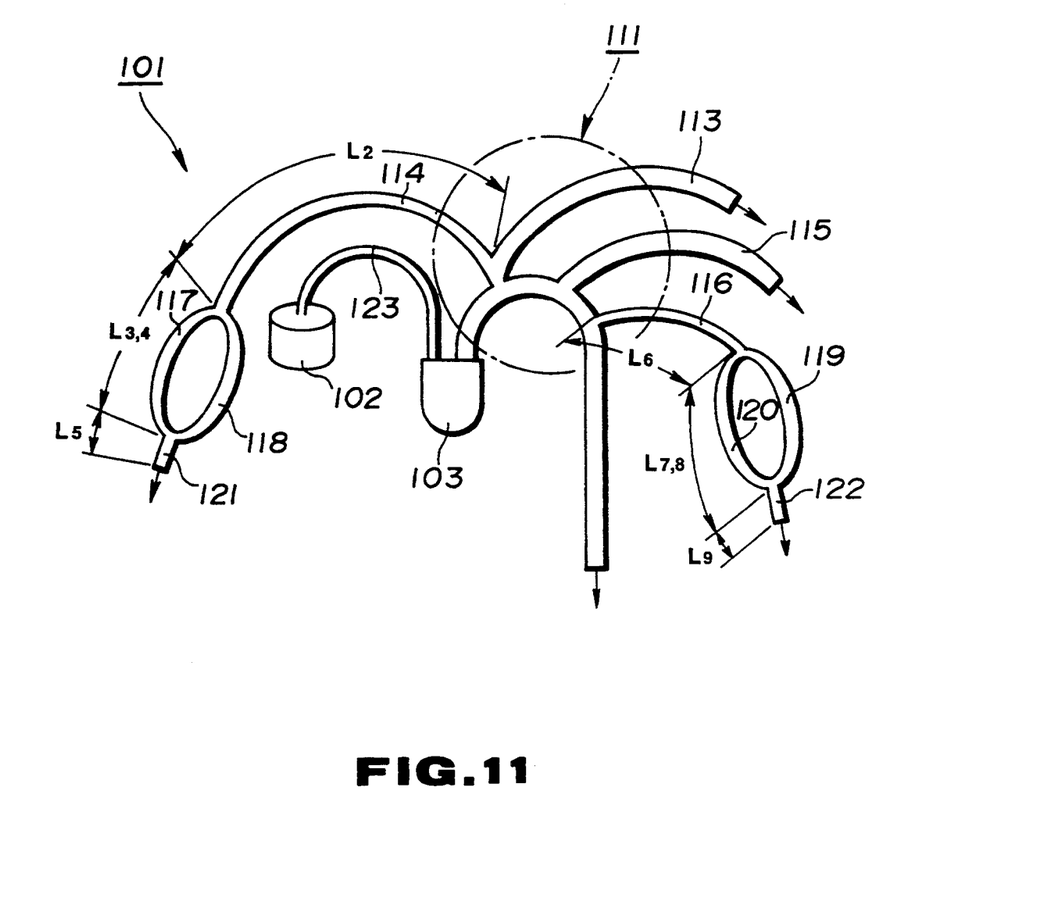
FIG. 11 is a view showing an example of a simulated blood circulating passage of the simulated blood circulating apparatus shown in FIG. 10.
Figure 12:
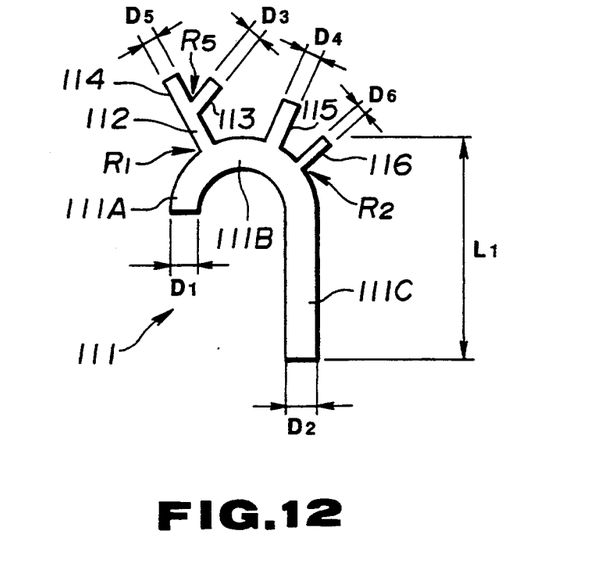
FIG. 12 is a view showing the arch of the aorta portion in the simulated blood circulating passage shown in FIG. 11.

The simulated blood circulating passage 101 is formed of tube having circular section of a rubber resin (silicon and natural rubbers) in which the wall thickness of the tube, Young Modulus, tensile strength, dimension and compliance are preset to adapt to simulation of a human body and comprises the arch of the aorta portion 111, the brachiocephalic artery portion 112, the right common carotid artery portion 113, the right subclavian artery portion 114, the left common carotid artery portion 115, the left subclavian artery portion 116, the right ulnar artery portion 117, the right radial artery portion 118, the left ulnar artery portion 119, the left radial artery portion 120, the right hand artery portion 121, and left hand artery portion 122, corresponding to the arch of the aorta, the left brachiocephalic, artery, the right common carotid artery, the right subclavian artery, the left common carotid artery, the left subclavian artery, right ulnar artery, the right radial artery, the left ulnar artery, left radial artery, the right hand artery, the left hand artery and the superior and inferior vein, respectively as shown in FIGS. 11 and 12.

In other words, the arch of the aorta portion 111 which is connected with the artificial heart unit 103 comprises a connection portion 111A having an inner diameter $D_1$ of 27.5 mm, a curved portion 111B extending from the connection portion 111A having a curvature radius $R_1$ and a downward depending portion 111C extending from the curved portion 111B and at a curvature radius $R_2$ and having an inner diameter $D_2$ of 17.5 min. The arch of the aorta 111 are 1.5 mm, 2.0 mm, and 2.5 mm in wall thickness. The length $L_1$ between the top of the curved portion 111B and the lower end of the downward depending portion 111C is 200 min. The arch of the aorta portion 111 is branched at the curved portion 111B into the brachiocephalic portion 1112, the left common carotid artery portion 115 and the left subclavian artery portion 116 and the brachiocephalic portion 112 is branched at the top thereof into the right common carotid artery portion 113 and the right subclavian artery portion 114. The inner diameters $D_3$ and $D_4$ of the right and left common carotid artery portions 113 and 114 are 11 mm. The inner diameter $D_5$ and $D_6$ of the right and left subclavian artery portions 114 and 116 are 8 mm.

The right subclavian portion 114 is formed so that it has a length $L_2$ of 550 mm and is branched at the tip end thereof into the right ulnar artery portion 117 and right radial artery portion 118 which have lengths $L_3$ and $L_4$ of 350 mm, respectively and is connected at the tip ends thereof with the right hand artery portion 121. The length $L_5$ of the right hand artery 121 is 700 mm.

The left subclavian portion 116 is formed so that it has a length $L_6$ of 420 mm and is branched at the tip end thereof into the left ulnar artery portion 119 and left radial artery portion 120 which have lengths $L_7$ and $L_8$ of 350 mm, respectively and is connected at the tip ends thereof with the left hand artery portion 122. The length $L_9$ of left hand artery 121 is 700 mm.

The right subclavian artery portion 114 simulates the right subclavian artery and the axillary artery and the brachial artery similarly the left subclavian artery portion 116 simulates the left subclavian portion 116, the axillary artery and the brachial artery. The right ulnar artery portion 117 and right radial artery 118 simulate, at the connection portion with the right hand artery portion 121, the superficial palmer venous arch and the deep palmer arch. Similarly, the left ulnar artery portion 119 and left radial artery portion 120 simulated, at the connection portion with the left hand artery portion 122, the superficial palmer venous arch and the deep palmer arch.

The simulated blood circulating passage 101 having such a structure is supported on a stand 105 in a substantially horizontal manner as shown in FIG. 10. The downward depending portion 11C of the arch of the aorta 111, the right common carotid artery portion 113 and the left common carotid artery portion 115 have respective outlet portions at the tip ends thereof which are introduced into the vein reservoir 106. The right and left hand artery portions 121 and 122 have respective outlet portion at the tip ends thereof, which are introduced into the vein portion reservoir 107. Clips 131, 132, 133, 134 and 135, the gripping forces of which are adjustable by screwing are mounted on the downward depending portion 111C of the arch of the aorta portion 111, the right and left common carotid artery portions 113 and 115, the right and left hand artery portions 121 and 122 in the vicinity of the respective outlets at the tip ends thereof so that the resistances of the respective passages can be variably preset by the clips 131 , 132, 133, 134 and 135, respectively. Clips 141, 142 and 143, 144, the gripping forces preset by spring members are mounted on the right and left subclavian artery portions 114 and 116 so that the resistances of the respective passages are preset by the clips 141, 142 and 143, 144, respectively.

The pipe 123 of the simulated blood circulating passage 101 is connected with the artificial heart unit 103 to form a passage for supplying simulated blood reserved in the atrium reservoir 102 to the artificial heart unit 3. The atrium reservoir 102 is replenished with simulated blood via a replenishing pipe 108.

The artificial heart unit 103 is driven by supplying driving compressed air from the artificial heart driving unit 104, the artificial heart unit 103 pumps out simulated blood which is supplied from the atrium reservoir 102 through the pipe 23 into the arch of the aorta portion 111 of the simulated blood circulating passage 101.

In the thus formed simulated blood circulating apparatus, the simulated blood is supplied to the simulated blood circulating passage 101 from the artificial heart unit 103 by driving the artificial heart unit 103. The simulated blood which is supplied to the simulated blood circulating passage 101 is discharged to the vein reservoir 106 from respective outlets at the tip end thereof of the downward depending portion 111C of the arch of the aorta portion 111, the right and left common carotid artery portions 113 and 115 and from the right and left hand artery portions 121 and 122.

Figure 13:
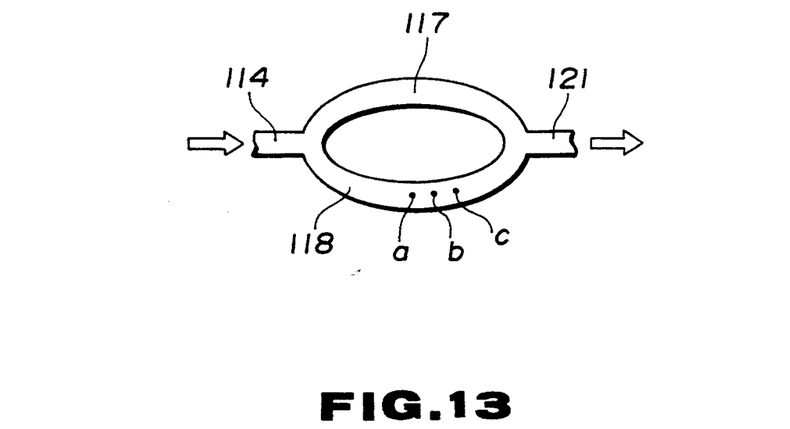
FIG. 13 is a view showing a measuring point where sphygmic diagnosis simulation of Oriental medicine is conducted by the simulated blood circulating apparatus shown in FIG. 10.

The passages of the arch of the aorta portion 111, the right brachiocephalic portion 112, the right subclavian artery portion 114 and the right ulnar artery portion 117, the right radial artery portion 118 and the right hand artery portion 121 of the simulated blood circulating passage 101 simulate the artery portion in the right hand of the blood circulating system of the human body. Sphygmic diagnosis simulation can be performed by measuring the arterial pulses in three points a, b and c of the right radial artery portion 118 corresponding to three positions of the shun, khan and shaku of the sunko in Oriental medicine. Similarly, the passages of the arch of the aorta portion 111, the left subclavian artery portion 116 and the left ulnar artery portion 119, the left ulnar artery portion 119, the left radial artery portion 120 and the left hand artery portion 122 of the simulated blood circulating passage 101 simulated the artery portion in the left hand of the blood circulating system of the human body. Sphygmic diagnosis simulation can be performed by measuring the arterial pulses in three points a, b and c of the left radial artery portion 119 corresponding to three positions of the shun, khan and shaku of the sunko in Oriental medicine.

As mentioned above, in the blood circulating function observing apparatus of the present invention, a notch contained in the detection output signal from the first pressure sensor which detects the arterial pulses on the heart side is detected by the first notch detecting circuit and a notch contained in the detection output signal from the second pressure sensor which detects the arterial pulses on the peripheral side on the blood flow passage limit condition in which a detection output signal having a predetermined level can be obtained by the second pressure sensor which detects the arterial pulses on the peripheral side. The blood circulating function observation data are obtained as notch occurrence time information and are outputted from the output means. Accordingly, the condition of the blood circulating function of the patient can be properly diagnosed in a noncontact manner with blood without any experience.

In the blood viscosity observing apparatus of the present invention, the blood viscosity observing data which are quantified as the time difference between the time when the detection output signal is obtained by the first pressure sensor which detects the arterial pulses on the heart side and the time detection output signal is obtained by the second pressure sensor which detects the arterial pulses on the peripheral side are obtained and outputted from the output means on the blood flow passing limit condition in which the detection output signal having a predetermined level is obtained by the second pressure sensor which detects the arterial pulses on the peripheral side. Hence the blood viscosity of the patient can be properly diagnosed in a non-contact manner with blood without any experience. Information on the blood viscosity can be used for the diagnosis of the internal organs.

The blood flow passage limitation is conducted at the same pressure in three positions which are closely positioned along the artery in the artery hardness observing apparatus of the present invention. The arterial pulses in the intermediate and peripheral positions of the three biasing positions which are closed disposed along the artery are detected by the first and second pressure sensors, respectively. The biasing force exerted by biasing means to restrict the blood flow is detected by the third pressure sensor. The detection signal representative of the difference in level between the detection output signals which are obtained by the third pressure sensors on the blood flow passage restricted conditions in which the first and second pressure sensors obtain detection output signals having predetermined levels can be obtained as observation information on the quantified hardness of the artery. Since the observation information on the hardness of the artery is outputted from the output means, the hardness of artery of the patient can be properly diagnosed in a non-contact manner with blood without any experience. Accordingly, the information on the hardness of the artery can be used for the diagnosis of the heart disease.

What is claimed is:

1. An apparatus for observing and evaluating blood circulation, comprising:

first and second pressure sensors adapted to be disposed along an artery outputting respective first and second pressure signals, wherein, the first pressure sensor is adapted to detect an artery pulse in said artery on a heart side and the second pressure sensor is adapted to detect said artery pulse between said heart side and a peripheral side;

a first level detecting means for detecting when the first pressure signal exceeds a predetermined level and providing an output signal representative thereof;

a second level detecting means for detecting when the second pressure signal exceeds a predetermined level and providing an output signal representative thereof;

biasing pressure controlling means responsive to the output of the second level detecting means for controlling the biasing force exerted by a biasing means; wherein, said biasing means is adapted to exert said biasing force upon the blood flow through the artery;

measuring means for measuring a first period of time after the first level detecting means detects that the first pressure signal exceeds a predetermined level and a second period of time from when a notch occurs in the first pressure signal until a notch occurs in the second pressure signal; and outputting means for outputting an output signal from said measuring means.

2. The apparatus for observing and evaluating blood circulation as defined in claim 1 in which said measuring means comprises:

a first notch detecting means for detecting the notch in the first pressure signal and providing an output signal;

a second notch detecting means for detecting the notch in the second pressure signal and providing an output signal;

a first timer means which starts measuring in response to the output signal from said first level detection means and terminates measuring in response to the output signal from said first notch detecting means; and second timer means which starts measuring in response to the output signal from said first level detecting means and terminates measuring in response to the output signal from the second notch detecting means.

3. The apparatus for observing and evaluating blood circulation as defined in claim 2, wherein said first and second notch detecting means each comprise a subtractor having one input connected to a low pass filter means for extracting a fundamental wave component from the respective first or second pressure signals, and another input receiving the respective first or second pressure signal.

4. The apparatus for observing and evaluating blood circulation as defined in claim 1, wherein the biasing pressure controlling means gradually lowers the biasing force from a high pressure blocking blood flow to a lower pressure allowing blood flow and maintains a substantially constant restricted blood flow passage condition in response to the output signal of the second level detecting means.

5. The apparatus for observing and evaluating blood circulation as defined in claim 4, wherein the outputting means provides output signals indicative of the functioning of the blood circulation, whereby the detection by the measuring means of a notch in at least the first or second pressure signal indicates an abnormal blood circulation function.

6. The apparatus for observing and evaluating blood circulation as defined in claim 1, wherein the outputting means provides output signals indicative of the functioning of the blood circulation, whereby, the detection by the measuring means of a notch in at least the first or second pressure signal indicates an abnormal blood circulation function.

7. The apparatus for observing and evaluating blood circulation as defined in claim 6, wherein the outputting means outputs a signal indicating an abnormality of fast pressure propagation due to a valve abnormality when the measuring means measures that the notch in the first pressure signal and the notch in the second pressure signal occur at substantially the same time.

8. The apparatus for observing and evaluating blood circulation as defined in claim 6, wherein the outputting means outputs a signal indicating an abnormality of slow propagation flow due to a heart muscle abnormality when the measuring means detects the second time period with a time difference between the occurrences of the notches in the first and second pressure signals.

9. The apparatus for observing and evaluating blood circulation as defined in claim 1, wherein said measuring means further comprises a means for detecting a notch in the first pressure signal and an integrating means connected to said means for detecting a notch in the first pressure signal;

said integrating means providing an integrated notch signal to the output means; and said output means outputting a signal indicative of the size of the notch in the first pressure signal.

10. The apparatus for observing and evaluating blood circulation as defined in claim 9, wherein said outputting means outputs a signal indicating a disease condition based on the integrated notch signal.

11. The apparatus for observing and evaluating blood circulation as defined in claim 1, wherein said first pressure sensor is adapted to be positioned at a first spot along said artery to detect pulses at the shun of the sunko, and said second pressure sensor is adapted to be positioned at a second spot along said artery to detect pulses at the khan of the sunko, wherein, said first spot at the shun of the sunko corresponds substantially to a spot on the heart side of said artery on the processus styloideus radii on the inner side of a wrist and said second spot at the khan of the sunko corresponds substantially to a spot between said heart side and a distal end side of said artery on said processus styloideus radii on said inner side of said wrist.

12. The apparatus for observing and evaluating blood circulation as defined in claim 1, wherein the outputting means outputs an output signal from said measuring means comprising data indicative of an observed blood circulating function, whereby the data is obtained from information on the notch portions of the first and second pressure signals on a blood flow passage restricted condition in which the output signal from the second level detecting means is obtained.

13. A blood viscosity measuring apparatus, comprising:

first and second pressure sensors adapted to be disposed along an artery outputting respective first and second pressure signals, wherein the first pressure sensor is adapted to detect a pulse in the artery on a heart side and the second pressure sensor is adapted to detect said artery pulse between the heart side and a peripheral side;

a first level detecting means for detecting when the first pressure signal exceeds a predetermined level and providing an output signal representative thereof;

a second level detecting means for detecting when the second pressure signal exceeds a predetermined level and providing an output signal representative thereof;

biasing pressure controlling means responsive to the output of the second level detecting means for controlling the biasing force exerted by a biasing means; wherein, said biasing means is adapted to exert said biasing force upon the blood flow through said artery;

timer means which starts measuring in response to the output signal from said first level detecting means and terminates measuring in response to the output signal from said second level detection means and provides an output signal; and outputting means which receives the output signal from the timer means and outputs an output signal; whereby said output signal from said outputting means provides blood viscosity information based on said output signal from said timer means.

14. The blood viscosity measuring apparatus as defined in claim 13, wherein said first pressure sensor is adapted to be positioned at a first spot long said artery to detect pulses at the shun of the sunko and said second pressure sensor is adapted to be positioned at a second spot along said artery to detect pulses at the khan of the sunko, wherein, said first spot at the shun of the sunko corresponds to a spot on the heart side of said artery on the processus styloideus radii on the inner side of a wrist and said second spot at the khan of the sunko corresponds to a spot between said heart side and distal end side of said artery on said processus styloideus radii on said inner side of said wrist.

15. The blood viscosity measuring apparatus as defined in claim 13, wherein said outputting means further obtains information on the blood viscosity by normalizing the detected blood viscosity.

16. The blood viscosity measuring apparatus as defined in claim 13, wherein said blood viscosity information indicates the state of internal organs.

17. The blood viscosity measuring apparatus as defined in claim 13, wherein the outputting means outputs an output signal indicating blood viscosity measurement data, whereby, the blood viscosity measurement data is obtained from the first and second pressure signals on a blood flow passage restricted condition in which the output signal from the second level detecting means is obtained.

18. An artery hardness observing apparatus, comprising:
  biasing means for exerting a biasing force, whereby, said biasing means restricts the flow of blood at three biasing positions closely located along an artery at about the same pressure;
  biasing controlling means for controlling the biasing force exerted by said biasing means;
  first and second pressure sensors, wherein, said first pressure sensor is adapted to detect arterial pulses in an intermediate position of the three biasing positions and to provide an output signal representative thereof, and said second pressure sensor is adapted to detect arterial pulses on a peripheral side of said first pressure sensor and to provide an output signal representative thereof;
  a third pressure sensor, detecting the biasing force exerted by said biasing means and providing an output signal representative thereof;
  a first level detecting means for detecting when the output signal from the first pressure sensor exceeds a predetermined level and for providing an output signal representative thereof;
  a second level detecting means for detecting when the output signal from the second pressure sensor exceeds a predetermined level and for providing an output signal representative thereof;
  operating means for operating a difference between a first latch output signal which is obtained by latching the output signal from the third pressure sensor in response to the output signal from said first level detecting means and a second latch output signal which is obtained by latching the output signal from the third pressure sensor in response to the output signal from said second level detecting means; and
  outputting means for outputting an output signal from said operating means, whereby, said output signal is indicative of artery hardness.

19. An artery hardness observing apparatus as defined in claim 18 in which said operating means comprises:
  a first latching means latching the output signal from said third pressure sensor in response to the output signal from said first level detecting means and providing the first latch output signal;
  a second latching means for latching the output signal from said third pressure sensor in response to the output signal from said second level detecting means and providing the second latch output signal; and
  difference detecting means for detecting a difference between the first and second latch output signals from said first and second latching means.

20. An artery hardness observing apparatus as defined in claim 18 in which said operating means divides the difference between the first latch output signal and the second latch output signal, by the first latch output signal.

21. The artery hardness observing apparatus as defined in claim 18, wherein said three biasing positions correspond to shun, khan, and shaku spots on the sunko, said first pressure sensor is adapted to be positioned to detect pulses at the khan of the sunko and said second pressure sensor is adapted to be positioned to detect pulses at the shaku of the sunko, wherein, said shun, khan, and shaku spots on the sunko correspond substantially to spots on the processus styloideus radii on the inner side of a wrist with said shun spot being on the heart side, said khan spot being between said heart side and a distal end side, and said shaku spot being on said distal end side.

22. The artery hardness observing apparatus as defined in claim 18, wherein the outputting means outputs an output signal from the operating means as observing information on the artery hardness, whereby the information on the artery hardness is obtained based upon output signals from said third pressure sensor indicating the blood flow passage restricted conditions in which the output signals are obtained from said first and second level detecting means.

23. An apparatus for observing the condition of the inner wall of blood vessels, comprising:
  first and second pressure sensors adapted to be disposed along an artery outputting respective first and second pressure signals, wherein, the first pressure sensor is adapted to detect a pulse in the artery on a heart side and the second pressure sensor is adapted to detect an artery pulse between the heart side and a peripheral side;
  level detecting means for detecting when the second pressure signal exceeds a predetermined level and providing an output signal representative thereof;
  biasing controlling means for controlling the biasing force exerted by a biasing means, said biasing means being adapted to establish a restricted blood flow passage condition based on the output signal obtained from said level detecting means; and
  outputting means for outputting a comparison output signal between a reference waveform signal based upon the first pressure signal and the second pressure signal.

24. The apparatus for observing the condition of the inner wall of blood vessels as defined in claim 23, wherein said first pressure sensor is adapted to be positioned to detect pulses at the shun of the sunko and said second pressure sensor is adapted to be positioned to detect pulses at the khan of the sunko, wherein, said shun of the sunko corresponds substantially to a spot on the heart side of said artery on the processus styloideus radii on the inner side of a wrist and said khan of the sunko corresponds substantially to a spot between said heart side and a distal end side of said artery on said processus styloideus radii on said inner side of said wrist.

25. The apparatus for observing the condition of the inner wall of blood vessels as defined in claim 23, wherein the comparison output signal includes observing information on the condition of the inner wall of the blood vessel, whereby, the observing information on the condition of the inner wall of the blood vessel is obtained from the second pressure signal on a blood flow passage restricted condition in which an output signal is obtained from said level detecting means.

26. An apparatus for observing and evaluating blood circulation, comprising:
- first, second, and third pressure sensors adapted to be disposed along an artery outputting respective first, second and third pressure signals, wherein, the first pressure sensor is adapted to detect a pulse in the artery on a heart side, the second pressure sensor is adapted to detect an artery pulse between the heart side and a peripheral side, and the third pressure sensor is adapted to detect an artery pulse on the peripheral side of the second pressure sensor;
- a first level detecting means for detecting when the first pressure signal exceeds a predetermined level and for providing an output signal representative thereof;
- a second level detecting means for detecting when the second pressure signal exceeds a predetermined level and for providing an output signal representative thereof;
- a third level detecting means for detecting when the third pressure signal exceeds a predetermined level for providing an output signal representative thereof;
- a biasing means for exerting a biasing force;
- biasing pressure controlling means, responsive to the output signal of the second level detecting means, for controlling the biasing force exerted by said biasing means; wherein, said biasing means is adapted to exert said biasing force upon the blood flow through said artery;
- a fourth pressure sensor detects the biasing force exerted by the biasing means and outputs a fourth pressure signal;
- measuring means for measuring a first period of time after the first level detecting means detects that the first pressure signal exceeds a predetermined level and a second period of time from when a notch occurs in the first pressure signal until a notch occurs in the second pressure signal;
- operating means for operating a difference between a first latch output signal which is obtained by latching the fourth pressure signal in response to the output signal from said second level detecting means and a second latch output signal which is obtained by latching the fourth pressure signal in response to the output signal from said third level detecting means;
- timer means for starting measuring in response to the output signal from said first level detecting means and terminating measuring in response to the output signal from said second level detection means and for providing an output signal; and
- outputting means for outputting output signals from said measuring means, said operating means, and said timer means.

* * * * *